US012653768B2

(12) United States Patent
Raths et al.

(10) Patent No.: US 12,653,768 B2
(45) Date of Patent: Jun. 16, 2026

(54) POLYOL ESTER MIXTURE FOR USE AS VASELINE SUBSTITUTE

(71) Applicant: BASF SE, Ludwigshafen (DE)

(72) Inventors: Hans-Christian Raths, Monheim (DE); Almud Folge, Düsseldorf (DE); Dagmar Stahlhut-Behn, Düsseldorf (DE); Björn Thomas Hahn, Düsseldorf (DE); Stefan Busch, Düsseldorf (DE)

(73) Assignee: BASF SE, Ludwigshafen am Rhein (DE)

( * ) Notice: Subject to any disclaimer, the term of this patent is extended or adjusted under 35 U.S.C. 154(b) by 286 days.

(21) Appl. No.: 18/576,499

(22) PCT Filed: Jul. 1, 2022

(86) PCT No.: PCT/EP2022/068226

§ 371 (c)(1),
(2) Date: Jan. 4, 2024

(87) PCT Pub. No.: WO2023/280694

PCT Pub. Date: Jan. 12, 2023

(65) Prior Publication Data

US 2024/0325268 A1 Oct. 3, 2024

(30) Foreign Application Priority Data

Jul. 9, 2021 (EP) .................................... 21184868

(51) Int. Cl.
*A61K 8/37* (2006.01)
*A61Q 19/00* (2006.01)

(52) U.S. Cl.
CPC ................ *A61K 8/37* (2013.01); *A61Q 19/00* (2013.01)

(58) Field of Classification Search
CPC .................................. A61K 8/37; A61Q 19/00
USPC .......................................................... 514/785
See application file for complete search history.

(56) References Cited

U.S. PATENT DOCUMENTS

| | | | |
|---|---|---|---|
| 7,037,439 | B2 | 5/2006 | Tavares |
| 2009/0192233 | A1 | 7/2009 | Brinkmann |
| 2019/0255180 | A1 | 8/2019 | Gabriele et al. |

FOREIGN PATENT DOCUMENTS

| | | | |
|---|---|---|---|
| DE | 2904164 | A1 | 8/1980 |
| DE | 19712033 | A1 | 9/1998 |
| EP | 0693471 | B1 | 1/1998 |
| EP | 0694521 | B1 | 1/1998 |
| EP | 0818450 | A1 | 1/1998 |
| EP | 1962790 | A1 | 9/2008 |
| EP | 2011483 | A2 | 1/2009 |
| EP | 2048178 | A1 | 4/2009 |
| EP | 2779991 | A2 | 9/2014 |
| EP | 2814453 | A1 | 12/2014 |
| EP | 2814800 | A1 | 12/2014 |
| JP | 2000-204060 | A | 7/2000 |
| WO | WO-2006/004911 | A2 | 1/2006 |

OTHER PUBLICATIONS

European Search Report for EP Patent Application No. 21184868.4, Issued on Jan. 31, 2022, 3 pages.
International Application No. PCT/EP2022/068226, International Search Report and Written Opinion, mailed Oct. 19, 2022.

*Primary Examiner* — Kristin A Vajda
(74) *Attorney, Agent, or Firm* — Faegre Drinker Biddle & Reath LLP

(57) ABSTRACT

A polyolester mixture as substitute for vaseline obtainable by esterification reaction of a) 0.8 to 1.2 mol glycerin b) 0.5 to 0.7 mol sebacic acid c) 1.0 to 1.4 mol of a monocarboxylic fatty acid mixture with a chain length of 8 to 24 carbon atoms characterized in that the fatty acid mixture c) comprises at maximum 30 wt % of a linear C18 fatty acid, at maximum 3 wt % of fatty acids lower than C12 and at maximum 3 wt % of fatty acids higher than C18 based on the weight of the sum of monocarboxylic fatty acids.

10 Claims, No Drawings

POLYOL ESTER MIXTURE FOR USE AS VASELINE SUBSTITUTE

CROSS-REFERENCE TO RELATED APPLICATIONS

This is the U.S. national phase of International Application No. PCT/EP2022/068226, filed Jul. 1, 2022, which claims the benefit of European Patent Application No. 21184868.4, filed Jul. 9, 2021.

FIELD OF THE INVENTION

The present invention relates to polyol ester mixtures which form a semisolid composition suitable as a replacement for petrolatum, their use in cosmetic and/or pharmaceutical preparations, and cosmetic and/or pharmaceutical preparations comprising these complex esters.

PRIOR ART

Petrolatum—also called vaseline—is an often used ointment base for many cosmetic and/or pharmaceutical applications. It is widely applied in leave-on and rinse-off preparations, as the basis of creams and ointments and can, for example, also be used in shower baths.

Petrolatum is a colorless to amber gelatinous semisolid hydrocarbon gel consisting of two-phases: 70 to 90% of a liquid phase of n- and isoparaffins and olefin hydrocarbons such as cetene, heptadecene and octadecene, and 10 to 30% of a solid phase with a microcrystalline fraction predominantly of isoparaffins and a crystalline fraction of n-paraffins. The characteristic rheological behavior of petrolatum and its melting profile results from the three-dimensional framework of different paraffins building crystalline, microcrystalline and liquid regions.

When applied to the body, especially topically onto the skin, which has a temperature of approximately 31° C., petrolatum provides an occlusive film which minimizes loss of water from tissues underlying the surface of the body into the environment; the water is thus accumulated in the stratum corneum Naturally obtained vaseline is a mixture of n-paraffins, isoparaffins and hydroaromatic hydrocarbons that is produced in the residue during the refining of petroleum and which is purified by treating with concentrated sulfuric acid and bleaching earths and/or activated carbon. Different grades of Vaseline are produced depending on the type of purification. However, there likewise also exists a synthetically produced Vaseline which is obtained by dissolving paraffin and ceresin in liquid paraffin. As a petroleum product, vaseline is not a "renewable raw material" and is undesired for environmental issues. Petroleum products usually contain mineral oil aromatic hydrocarbons (MOAH) as impurities which are known to be cancerogenic. In addition paraffins are known to accumulate, depending on chain length, in the liver, lymph nodes and kidneys. Time and again, it is discussed how mineral oils, that are difficult to degrade, lead to an accumulation in the body and, as a result of closing the skin pores, impair the breathing of the skin or promote the development of acne. Lipcare sticks containing mineral oils have therefore also already been criticized.

Hence already for many years it was an object to develop products to replace Vaseline, but which were made of renewable raw materials and are biodegradable. In terms of properties, they more or less correspond to those of vaseline.

EP2779991 A1 describes a mixture of beeswax in shea butter. With shea butter having a melting range of 34 to 46° C., the resulting composition must be distributed by vigorous rubbing to melt at 31° C. skin temperature. Furthermore, beeswax and sheabutter, being natural products, cannot in the short term be produced in large amounts and suffer from naturally derived differences in their physical properties.

EP 2011483 A1 discloses a mixture of 60% to 98% by weight of medium-chain triglycerides (MCT) with 2% to 40% by weight of long-chain triglycerides (LCT) as a replacement for petrolatum, which still needs the incorporation of a wax to have sufficient solidity at room temperature and form a water-insoluble layer that is mechanically stable.

In U.S. Pat. No. 7,037,439 a carrier with similar properties as Vaseline is prepared by suspending ultrafine particles of a waxy solid homogeneously distributed in a naturally occurring vegetable oil to form a homogeneous colloidal solution. However, a difficult two-step process is necessary to obtain the respective ointment base with the required petrolatum-like properties. In addition the sensory properties during melting on the skin are different to Vaseline due to the solid waxy particles melting at higher temperature.

EP2814453 A1 discloses a composition obtainable by condensation reaction of a) 25 to 90% by weight of unbranched fatty alcohols with a chain length of 12 to 18 carbon atoms, b) 5 to 50% by weight of isostearyl alcohol, c) 0 to 35% by weight of a fatty alcohol with a chain length of 20 and/or 22 carbon atoms and d) 0 to 25% by weight of a fatty alcohol having 8 and/or 10 carbon atoms wherein it has a melting range, measured by differential scanning calorimetry (DSC), between −25° C. and +70° C. Besides a high price of the raw materials, these ethers will not easily biodegrade.

EP 2814800 A1 discloses a Guerbet alcohol mixture obtainable by reacting a) 55 to 95% by weight of cetylstearyl alcohol, b) 5 to 45% by weight of unbranched, saturated fatty alcohols having the following chain distribution: C12 from 48-58%, C14 from 18-24%, C16 from 8-12%, C18 from 11-15%, and c) optionally 5% by weight of an aliphatic diol having at least 3 carbon atoms with the proviso that the mixture has a melting range, measured by differential scanning calorimetry (DSC), between −20° C. and +70° C., where the width of the melting range comprises at least 30 temperature degrees and the maximum of the melting range is 35±15° C., wherein the starting alcohols (a) to (c) are converted in a Guerbet reaction up to a conversion of 60 to 80%.

These complex ethers have a wide melting range with a maximum of the melting profile above 35° C. and were offered as substitute for Vaseline. However, sensory properties and the characteristics during application of ointments is depending on rheological properties while these are again depending on melting properties of a composition.

Although differential scanning calorimetry (DSC) profiles of these substitute compositions are similar to petrolatum, their sensory properties are completely different during topical application due to the different rheological properties at skin temperature. As the temperature of the skin is approximately 31° C., another object of the invention was a transition from solid-like properties to more liquid-like properties at skin temperature and improved sensory characteristics during and after topical application.

A few years ago complex esters obtained by reacting a polyol with diacids and monoacids have been developed as ointment bases for use in the cosmetic and pharmaceutical field.

According to WO 06/004911 a polyol polyester polymer has been manufactured comprising a reaction product of at least one polyfunctional alcohol with two to ten carbon atoms, at least one polyfunctional carboxylic acid, and at least one monofunctional carboxylic acid; wherein the polyfunctional carboxylic acid comprises one to about thirty-six carbon atoms and the monofunctional carboxylic acid comprises about four to twenty-four carbon atoms as replacement for castor oil. It has a similar viscosity and polarity to castor oil and is thus not suitable to be an ointment base to substitute petrolatum.

Similar polyol esters have been disclosed in European application EP1962790 A1 in form of a polyester oil obtainable by the reaction of a C4 to C10-dicarboxylic acid, a polyol and a C16 to C30-, particularly a C20 to C24-monocarboxylic fatty acid. The resulting ester mixture is a structurant, which can be used to provide structure, particularly thickening and/or gelling oils of a wide range of polarity. To be suitable as structurant for oils, especially castor oil, the monocarboxylic acid was preferably behenic acid, so that the melting behavior and rheological properties of the polyester oil was very different from vaseline.

A similar polyolester mixture which is as well used as a structuring and gelling agent is disclosed in EP2048178 A1. This esterification reaction product having a hydroxyl value is obtainable by subjecting component A selected from the group consisting of glycerin, trimethylolpropane, pentaerythritol, diglycerin and decaglycerin, component B selected from the group consisting of eicosanedioic acid, octadecanedioic acid and sebacic acid, component C selected from the group consisting of palmitic acid, stearic acid and behenic acid, and component D selected from isooctylic acid or isostearic acid, to an esterification reaction at 160 to 240° C. under an inert gas stream for 5 to 30 hours while removing water generated from the reaction, and using an acid catalyst or a metal catalyst, wherein the blending ratio of the respective components at the time of the esterification reaction are such that component A:component B=1.0 mole:0.10 to 0.20 moles, component A:component C=1.0 mole: 1.0 to 7.5 moles, and component A:component D=1.0 mole:0.2 to 2.3 moles.

While the disclosed polymer of EP1962790 A1 forms a solid waxy composition used as structuring agent for oils a similar ester made of fatty acids, glycerin and sebacic acid—offered under the name LexFilm™ Sun Natural MB (Inolex)—is a pourable viscous fluid. The capryloyl glycerin/sebacic acid copolymer is adapted to be used as a SPF boosting and water-resistant film-forming polymer for sun care applications and optimized to be compatible with organic and inorganic UV filters by a careful optimization of esterification conditions and carboxylic fatty acid distribution.

The same components to manufacture a polyol ester mixture have been used in Japanese application no. JP2000-204060A. The object of this invention was a substitute of vaseline which is dissolvable in castor oil. This was achieved by an esterification product of (1) 1 mol of glycerin, (2) 1 mol of one or more fatty acids selected from C8-28 linear fatty acids, branched fatty acids, unsaturated fatty acids, and hydroxy fatty acids, and (3) 2 mol of a linear or branched dibasic acid with an acid value of at least 50 mg KOH/g, characterized in that it was manufactured in a two-step reaction, where (1) and (2) are reacted, and (3) is furthermore reacted therewith until an acid value of at least 50 mg KOH/g is reached, so that the resulting product contains a reasonable amount of free fatty acids. It was stated that the present invention cannot be obtained outside the molar ratio of glycerol to monocarboxylic fatty acids to dicarboxylic fatty acid of 1:1:2. In order to achieve the desired properties a complicated two step process was necessary. As this product should have been dissolvable in castor oil the remaining acidic groups were necessary to reach sufficient solubility in castor oil, but a higher number of acidic groups results in disadvantages regarding the irritation potential in topical compositions. In case that part of the remaining free fatty acids result from short chain fatty acids a composition comprising these esters might have an unpleasant smell. In addition the method of manufacturing is time and cost intensive as it needs two separately conducted reactions.

There is still a need for biologically degradable hydrophobic ointment bases with similar properties as vaseline especially in consistency, rheology, spreadability, skin protection properties, physical stability, transparency and tolerability with other ointment components, but a reduced amount of irritable by-products and improved sensory properties. These ointment bases should be obtainable by a cost effective, environmentally friendly manufacturing process.

A composition melting at skin temperature is easier to apply and gives a sensorily advantageous impression. Owing to the site of application (often face and hands), increased demands are made on the sensory properties, especially a light feel, lower stickiness and waxiness during distribution.

DESCRIPTION OF THE INVENTION

These objects are solved with a polyolester obtainable by esterification reaction of a) 0.8 to 1.2 mol glycerol
b) 0.5 to 0.7 mol sebacic acid
c) 1.0 to 1.4 mol of a monocarboxylic fatty acid mixture with a chain length of 8 to 24 carbon atoms characterized in that the fatty acid mixture comprises at maximum 30 wt % of a linear C18 fatty acid, at maximum 3 wt % of fatty acids lower than C12 and at maximum 3 wt % of fatty acids higher than C18 based on the weight of the sum of monocarboxylic fatty acids.

The polyolester according to the present invention is an oligoester which is comparable with vaseline in terms of application properties but has improved sensorics and is obtained by a simple one-pot manufacturing method.

Surprisingly the selected molar ratio and the specific fatty acid distribution results in a polyol ester mixture with improved sensoric properties in view of stickiness, light feel and waxiness during distribution. Mainly the sensoric properties and improved distributing behavior results from rheological properties of the composition during melting. These can be characterized by oscillatory rheology at rising temperatures. Measuring the viscoelastic properties over a range of temperatures is an extremely sensitive technique for measuring the transition temperature of a material. In a temperature ramp, a linear heating rate is applied. Typical heating rates are on the order of 1 to 5° C./min. The material response is monitored at one or more frequencies, at constant amplitude within the linear-viscoelastic-rate (LVR).

Prior art documents often disclose the use of Differential Scanning Technology (DSC)—measurements in order to prove the similarity to vaseline by adapting the melting profiles. However, DSC-measurements (of the present inventive polyolester in comparison to prior art compositions) show a heatflow profile which could not be correlated with the melting behavior during application. While the ester compositions are still solid ointment like materials at 21 to 25° C. (approximate room temperature) the DSC-profiles already show a heatflow increase starting at approximately 0° C. (FIG. 1) with a maximum at about 10° C. (FIG. 1) which is interpreted as the maximum melting temperature.

Similar to an investigation by DSC oscillatory rheology yields the temperature-dependent properties of samples (usually polymers). Oscillatory rheology is a way of characterizing elastic solids—such as polymers—providing a characteristic profile of the material depending on mechanical stress at rising temperature. An important parameter obtained from these measurements is the loss tangent (also tan delta, therefore unitless) which is a measure for the dampening in a material at a given temperature: A loss tangent below 1 indicates the material to have more solid-like properties, while a loss tangent greater than 1 points to more liquid-like behaviour. Thus, it can be said that a loss tangent found during a temperature sweep to rise above 1 shows the material to gradually change from a solid-dominated to a liquid-dominated state, a loss tangent of 1 indicates balanced viscoelastic material properties.

The technique is better suited to simulate a rubbing on the skin during topical application and enables a better characterization of the polymer properties in view of its application properties.

Starting the evaluation below room temperature (25° C.±1° C.), e.g. at 15° C. and determining rheological changes at rising temperature up to 50° C. one can draw conclusions about the behavior of the oligomer at skin temperature of 31° C.±3° C. For the inventive polyolester the transition from solid-dominated to liquid-dominated is at skin temperature since the loss tangent was found to be 1 at about 31° C. (see FIG. 2). At room temperature and storage without a mechanical stress the polyester behaves like vaseline, but when topically applying the composition it is easier to distribute and has an improved sensoric feeling.

It is not possible to define the exact molecular structure of the polyol ester mixture since hydroxyl groups of the polyol and acidic groups of the dibasic and monocarboxylic acids can react in multiple ways to form an oligomer.

Accordingly the ester mixture is defined by the ratio of this raw materials. The molar ratio of glycerin to sebacic acid to monocarboxylic fatty acids is 0.8 to 1.2 glycerol to 0.5 to 0.7 sebacic acid to 1.0 to 1.4 monocarboxylic fatty acids, preferably it is 0.9 to 1.1 glycerol to 0.5 to 0.7 sebacic acid to 1.0 to 1.3 monocarboxylic fatty acids, most preferably 1 to 0.6 to 1.2. Hence a preferred polyol ester mixture is obtainable by esterification reaction of a) 0.9 to 1.1 mol glycerol
b) 0.5 to 0.7 mol sebacic acid
c) 1.1 to 1.3 mol of a monocarboxylic fatty acid mixture with a chain length of 8 to 24 carbon atoms, characterized in that the fatty acid mixture c) comprises at maximum 30 wt % of a linear C18 fatty acid, at maximum 3 wt % of fatty acids lower than C12 and at maximum 3 wt % of fatty acids higher than C18 based on the weight of the sum of monocarboxylic fatty acids.

Most preferably the polyol ester mixture is obtainable by esterification reaction of a) 1 mol glycerin, b) 0.6 mol sebacic acid and c) 1.2 mol of a monocarboxylic fatty acid mixture with a chain length of 8 to 24 carbon atoms, characterized in that the fatty acid mixture c) comprises at maximum 30 wt % of a linear C18 fatty acid, at maximum 3 wt % of fatty acids lower than C12 and at maximum 3 wt % of fatty acids higher than C18 based on the weight of the sum of monocarboxylic fatty acids.

The amount of free hydroxyl groups—defined by the hydroxyl value (HV) has an influence on the compatibility with further components in a cosmetic composition and sensoric properties due to differences of the hydrophilicity of the ester mixture.

A polyol ester mixture of the current invention is characterized in that it has an acid value below 5 mg KOH/g preferable below 3 mg KOH/g, more preferably below 2 mg KOH/g. In order to reach this value the molar ratio must be selected in a specific relation and the esterification reaction must be run up to completion, so that after esterification reaction almost no free acid groups remain in the product.

Monocarboxylic Fatty Acid Distribution

Most crucial for the sensory properties, melting behaviour and rheologic characteristics is the choice of the fatty acid distribution. The amounts of different fatty acids are determined by gas chromatography (fatty acids according to ISO 5508/5509, ISO 5508:1990 Animal and vegetable fats and oils—Analysis by gas chromatography of methyl esters of fatty acids; ISO 5509:2000 Animal and vegetable fats and oils—Preparation of methyl esters of fatty acids).

The fatty acid mixture c) comprises at maximum 30 wt % of a linear C18 fatty acid, at maximum 3 wt % of fatty acids lower than C12 and at maximum 3 wt % of fatty acids higher than C18 all % by weight based on the sum of monocarboxylic fatty acids in the reaction mixture.

The abbreviation "wt %" means "weight percentage" and is synonym to "% by weight". According to the invention all weight percentages denote the active matter weight percentage unless otherwise specified.

Preferably c) has the following distribution:
23 to 33 wt % of a linear C18 fatty acid,
20 to 28 wt % of a linear C16 fatty acid,
10 to 18 wt % of a linear C14 fatty acid and
30 to 40 wt % of a linear C12 fatty acid
with the proviso that the fatty acid mixture comprises at maximum 3 wt % of fatty acids lower than C12 and at maximum 3 wt % of fatty acids higher than C18, all % by weight based on the sum of monocarboxylic fatty acids in the reaction mixture.

More preferably c) has the following distribution:
25 to 29 wt % of a linear C18 fatty acid,
22 to 26 wt % of a linear C16 fatty acid,
12 to 16 wt % of a linear C14 fatty acid and
34 to 39 wt % of a linear C12 fatty acid
with the proviso that the fatty acid mixture comprises at maximum 3 wt % of fatty acids lower than C12 and at maximum 3 wt % of fatty acids higher than C18 all wt % based on the sum of monocarboxylic fatty acids in the reaction mixture.

Characterization of the Polyol Ester Mixture

TABLE 1

Most preferably the polyol ester mixture of the current invention has the following specification:

| | | preferably | most preferably | Test method |
|---|---|---|---|---|
| acid value | max. 5 mg KOH/g | max. 3 mg KOH/g | max. 2 mg KOH/g | ISO 660 |
| hydroxyl value | 55-90 mg KOH/g | 60-85 mg KOH/g | 65-80 mg KOH/g | ISO 4326 |
| saponification value | 270-330 mg KOH/g | 280-320 mg KOH/g | 290-310 mg KOH/g | ISO 3657 |
| water content | max. 3% | max. 2% | max. 1% | ISO 4317 (KF) |
| colour, 40° C. | max 250 Hazen | max 200 Hazen | max 150 Hazen | ISO 6271 |

Melting Range by DSC

For differential scanning calorimetry (tables 1a and b), the heat-flow DSC Q100 of TA Instruments (Waters GmbH) was used.

For each measurement, five to ten milligrams of the sample material were weighed into small aluminum pans and hermetically encapsulated (cold-sealed). These pans were subjected to a temperature ramp of −80° C. to +100° C. at a heating rate of 5 K/min and the heat-flow was analyzed. The results were measured reproducibly.

DSC—Profile

The invention provides polyol ester mixtures with a melting range, measured by differentical scanning calorimetry (DSC), between −25° C. and +60° C., preferably between, −15° C. and +50° C., more pref. −10° C. and +40° C., where the width of the melting range comprises at least 30° C. and the maximum of the heatflow (W g−1) is detected at 10±15° C., more preferably 10±10° C., most preferably 10±5° C.

The product properties of the polyol ester mixture were adjusted through optimization of the fatty acid composition, selection of the fatty acid distribution and implementation of the esterification reaction, meaning that the mixture is comparable to vaseline, but with improved application properties and has a comparable melting range when heated without applying stress.

As a result of fluctuations in the composition of vaseline, especially the different fractions of crystalline areas, the values ascertained using the precise method of DSC vary, meaning that the melting range ascertained for the polyolester mixture according to the invention is also in the temperature range between −25° C. and +70° C., preferably between −22° C. and +60° C. and particularly preferably between −20° C. and +55° C.

In this connection, the melting range does not have to span the entire width, but it should cover at least a range of 30° C. within the temperature range between −50° C. and +50° C.

Rheological Characterization

Due to the viscoelastic nature of polymers the properties of these compounds strongly depend on temperature and applied force. Viscoelasticity is a mixture of purely elastic solids in which the deformation is proportional to the applied force following Hooke's law and of viscous liquids in which the rate of deformation is proportional to the applied force accordant to Newton's law. Polymers behave in a more elastic fashion in response to a rapidly applied force and in a more viscous fashion when the force is applied in a slow manner.

Usually viscoelastic properties of polymers are analyzed in rheology. In the present investigations a rheometer with a parallel plate configuration was used in oscillatory mode. The polyol ester mixture (or vaseline) was placed on the plate of the rheometer. Torque and angular displacement are monitored at constant oscillating frequency and angular displacement at rising temperature. The measurement of the rheological properties especially for determining the loss tangent was conducted with a rheometer ARG2_10H4440 of TA Instruments (Geometry: Cross Hatched-40 mm parallel plate, Peltier plate Steel—104445; measurement conditions: 15 to 50° C.; 1K/min; 0.1% Strain; 1 Hz Frequency). The oscillatory rheology experiments yield complex dynamic shear modulus (G*), shear storage modulus (G'), shear loss modulus (G") and loss tangent (tan δ) (δ=phase angle, lag between stress and strain).

The loss tangent is calculated according to formula I:

$$\tan\delta = G''/G' \qquad \text{formula I}$$

The loss tangent below 1 characterises the elastic-dominant behaviour of the material and a loss tangent above 1 describes the viscous-dominant of the material, these properties vary with rising temperature. In addition the loss tangent is a sensitive indicator of cross-linking. Polymer chain entanglements act as temporary and relatively weak cross-links and damping decreases with an increasing degree of crosslinking.

Samples of neat vaseline and two polyolester mixtures with different fatty acid distribution have been investigated.

Surprisingly the loss tangent of the inventive polyol ester mixture was found at approximately 31° C. So that at skin temperature the elastic and viscous properties of the inventive polymer were equally balanced.

The polyol ester mixture according to the invention has a tangens delta of 1 at 31±5° C., preferably 31±3° C., most preferably 31±2° C. when determined by oscillatory rheology with a rheometer ARG2_10H4440 of TA Instruments (Geometry: Cross Hatched-40 mm parallel plate, Peltier plate Steel-104445; measurement conditions: 15 to 50° C.; 1 K/min; 0.1% Strain; 1 Hz Frequency).

Manufacturing the Polyol Ester Mixture

The polyol ester mixture of the invention can be manufactured by a generally conventional esterification, simply in a one step direct reaction charging glycerin, sebacic acid and the monoacid mixture to a reaction vessel and reacting these three components at elevated temperatures while removing the reaction water.

Hence another embodiment of the invention is a process of manufacturing a polyol ester mixture by reacting a) 0.8 to 1.2 mol glycerin, b) 0.5 to 0.7 mol sebacic acid and c) 1.0 to 1.4 mol of C8 to C24 monocarboxylic fatty acids, characterized in that the fatty acid mixture c) comprises at maximum 30 wt % of a linear C18 fatty acid, at maximum 3 wt % of fatty acids lower than C12 and at maximum 3 wt % of fatty acids higher than C18 based on the weight of the sum of monocarboxylic fatty acids without presence of a catalyst (or addition of a solvent) at a temperature of 180° C. to 250° C., under vacuum removing reaction water through a condenser, until the acid value is less than 5 mg KOH/g, preferably less than 3 mg KOH/g and more preferably less than 2 mg KOH/g.

The elevated reaction temperatures chosen is from 180 to 250° C., preferably from 200 to 240° C. and more preferably from 210 to 230° C. The reaction is carried out under vacuum in order to remove the reaction water.

Surprisingly it is not necessary to add any catalyst to the starting materials or any additional solvent, so that the manufacturing is completed by only adding the reactants a), b) and c) to the reaction vessel. Glycerol (component a)) serves as a dispersion medium in the beginning of the reaction, but cannot be considered as a solvent, it is one of the reacting components.

Since catalysts, for example Lewis and Brönsted acids such as tin oxide, tin oxalate, sulfonic acid, methanesulfonic acids, trifluoromethanesulfonic acids, phosphoric acids, or any alkali metal or alkaline earth metal alkoxide are not used, the manufacturing process is especially environmentally friendly.

Another embodiment of the invention is a process of manufacturing a polyol ester mixture in a "one-pot-process" by reacting a) 0.8 to 1.2 mol glycerin,
b) 0.5 to 0.7 mol sebacic acid and
c) 1.0 to 1.4 mol of C8 to C24 monocarboxylic fatty acids, characterized in that the fatty acid mixture c) comprises at maximum 30 wt % of a linear C18 fatty acid, at maximum 3 wt % of fatty acids lower than C12 and at maximum 3 wt % of fatty acids higher than C18 based on the weight of the sum of monocarboxylic fatty acids without presence of a catalyst and without addition of a solvent to the starting materials a), b) and c), at a temperature of 180 to 250° C., preferably 200 to 240° C. under vacuum removing reaction water through a condenser, until the acid value is less than 5 mg KOH/g, preferably less than 3 mg KOH/g and more preferably less than 2 mg KOH/g.

Use of the Polyolester

Due to their physical, chemical and in particular rheological properties, the polyol ester mixture can be used to replace vaseline in cosmetic, personal care or pharmaceutical preparations. Compared to vaseline the polyol ester mixture of the invention can be used as pure ointment base without addition of further emollients, oils or in combination with other components.

Cosmetic Preparations

The polyolester mixtures according to the invention are suitable as a base in pharmaceutical preparations for topical application and cosmetic compositions for bodycare and cleaning in personal care, skin care and hair care compositions, such as e.g. body oil, baby oil, body milk, creams, lotions, sprayable emulsions, sun protection compositions and antiperspirants. They can also be used in surfactant-containing preparations such as e.g. liquid soaps and bar soaps, foam and shower baths, hair shampoos and hair rinses. Also possible is use as care component on tissues, papers, wipes, nonwoven products, sponges, puffs, plasters and bandages which are widespread in the hygiene and care sector (wet wipes for baby hygiene and babycare, cleansing wipies, face cleansing wipes, skincare wipes, care wipes with active ingredients to combat skin aging, wipes with sun protection formulations and insect repellants, and also wipes for decorative cosmetics or for after-sun treatment, toilet wet wipes, antiperspirant wipes, diapers, pocket tissues, wet wipes, hygiene products, self-tanning wipes). They can also be used inter alia in preparations for haircare, hair cleaning or hair coloring. They can furthermore be used in preparations of decorative cosmetics, such as, for example, lipsticks, lip gloss, make-up, foundations, powders, eyeshadows, mascara and the like.

The use concentrations in the respective formulations and preparations are comparable to those of vaseline. The pharmaceutical and cosmetic preparations comprising the polyol ester mixture according to the invention are therefore likewise provided by the invention.

The inventive polyolester mixtures can be used in concentrations of 0.5 wt % up to 100 wt %, preferably 1 to 50 wt %, more preferably 2 to 20 wt % and most preferably 2.5 to 15 wt % based on the weight of the cosmetic or pharmaceutical composition.

Hence another embodiment of the invention are cosmetic or pharmaceutical compositions comprising 0.5 wt % up to 100 wt %, preferably 1 to 50 wt %, more preferably 2 to 20 wt % and most preferably 2.5 to 15 wt % of the polyol ester mixture according to the invention based on the weight of the cosmetic or pharmaceutical composition.

Since the polyol ester mixture according to the invention, especially in surface-active preparations, have advantages over using vaseline by virtue of the fact that the amount of foam is greater than in comparable vaseline-containing systems, cosmetic and/or pharmaceutical preparations comprising the polyolester according to the invention and interface-active substances are also provided by the invention.

Depending on the application purpose, the cosmetic formulations comprise a series of further auxiliaries and additives, such as, for example, surfactants, further oil components, emulsifiers, pearlescent waxes, consistency regulators, thickeners, superfatting agents, stabilizers, polymers, fats, waxes, lecithins, phospholipids, biogenic active ingredients, UV light protection factors, antioxidants, deodorants, antiperspirants, antidandruff agents, film formers, swelling agents, insect repellants, self-tanning agents, tyrosinase inhibitors (depigmentation agents), fillers, hydrotropes, solubilizers, preservatives, perfume oils, dyes etc., which are listed below by way of example.

Suitable interface-active substances are in principle any substances which lower the surface tension between the aqueous and nonaqueous phases. Interface-active substances comprise emulsifiers and surfactants.

Nonionic Emulsifiers

The group of nonionic emulsifiers includes, for example:

(1) Addition products of from 2 to 50 mol of ethylene oxide and/or 1 to 20 mol of propylene oxide onto linear fatty alcohols having 8 to 40 carbon atoms, onto fatty acids having 12 to 40 carbon atoms and onto alkylphenols having 8 to 15 carbon atoms in the alkyl group.
(2) $C_{12}$-$C_{18}$-Fatty acid mono- and diesters of addition products of from 1 to 50 mol of ethylene oxide onto glycerol.
(3) Sorbitan mono- and diesters of saturated and unsaturated fatty acids having 6 to 22 carbon atoms and ethylene oxide addition products thereof.
(4) Alkyl mono- and oligoglycosides having 8 to 22 carbon atoms in the alkyl radical and ethoxylated analogs thereof.
(5) Addition products of from 7 to 60 mol of ethylene oxide onto castor oil and/or hydrogenated castor oil.
(6) Polyol and in particular polyglycerol esters, such as e.g. polyol poly-12-hydroxystearates, polyglycerol polyricinoleate, polyglyceryl-4 laurates, polyglycerol diisostearate or polyglycerol dimerate. Likewise of suitability are mixtures of compounds of two or more of these substances classes, such as e.g. polyglyceryl-4 diisostearates/polyhydroxystearates/sebacates.
(7) Addition products of from 2 to 15 mol of ethylene oxide onto castor oil and/or hydrogenated castor oil.
(8) Partial esters based on linear, branched, unsaturated or saturated $C_6$-$C_{22}$-fatty acids, ricinoleic acid and 12-hydroxystearic acid and polyglycerol, pentaerythritol, dipenta-erythritol, sugar alcohols (e.g. sorbitol), alkyl glucosides (e.g. methylglucoside, butylglucoside, laurylglucoside), and polyglucosides (e.g. cellulose), or mixed esters, and also sucrose polystearates (commercially available as Emulgade® SUCRO, BASF).
(9) Polysiloxane-polyalkyl-polyether copolymers and corresponding derivatives.
(10) Mixed esters of pentaerythritol, fatty acids, citric acid and fatty alcohol and/or mixed esters of fatty acids having 6 to 22 carbon atoms, methylglucose and polyols, preferably glycerol or polyglycerol.

The addition products of ethylene oxide and/or of propylene oxide onto fatty alcohols, fatty acids, alkylphenols, glycerol mono- and diesters, and also sorbitan mono- and diesters of fatty acids or onto castor oil are known, commercially available products. These are homolog mixtures, the average degree of alkoxylation of which corresponds to the ratio of the quantitative amounts of ethylene oxide and/or propylene oxide and substrate with which the addition reaction is carried out. They are W/O or O/W emulsifiers depending on the degree of ethoxylation. $C_{12/18}$-Fatty acid mono- and diesters of addition products of ethylene oxide onto glycerol are known as refatting agents for cosmetic preparations.

Suitable lipophilic W/O emulsifiers are in principle emulsifiers with an HLB value of 1 to 8, which are summarized in numerous tabular works and are known to the person skilled in the art. For ethoxylated products, the HLB value can also be calculated according to the following formula: HLB=(100−L): 5, where L is the weight fraction of the lipophilic groups, i.e. of the fatty alkyl or fatty acyl groups in percent by weight in the ethylene oxide adducts.

From the group of W/O emulsifiers, partial esters of polyols, in particular of $C_4$-$C_6$-polyols, are particularly advantageous, such as, for example, partial esters of pentaerythritol or sugar esters, e.g. sucrose distearate, sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Suitable emulsifiers are also addition products of 1 to 30, preferably 5 to 10, mol of ethylene oxide onto the specified sorbitan esters.

Depending on the formulation, it may be advantageous to additionally use at least one emulsifier from the group of nonionic O/W emulsifiers (HLB value: 8-18) and/or solubilizers. These are, for example, the ethylene oxide adducts already mentioned in the introduction and having a correspondingly high degree of ethoxylation, e.g. 10-20 ethylene oxide units for O/W emulsifiers and 20-40 ethylene oxide units for so-called solubilizers. According to the invention, ceteareth-12, ceteareth-20 and PEG-20 stearate are particularly advantageous as O/W emulsifiers. Suitable solubilizers are preferably Eumulgin® HRE 40 (INCI: PEG-40 hydrogenated castor oil), Eumulgin® HRE 60 (INCI: PEG-60 hydrogenated castor oil), Eumulgin® L (INCI: PPG-1-PEG-9 lauryl glycol ether), and Eumulgin® SML 20 (INCI: Polysorbate-20).

Nonionic emulsifiers from the group of alkyl oligoglycosides are particularly skin-friendly and therefore preferably suitable as O/W emulsifiers. $C_8$-$C_{22}$-Alkyl mono- and oligoglycosides, their preparation and their use are known from the prior art. Their preparation takes place in particular by reacting glucose or oligosaccharides with primary alcohols having 6 to 24, preferably 8 to 22, carbon atoms. As regards the glycoside radical, it is the case that both monoglycosides, in which one cyclic sugar radical is glycosidically bonded to the fatty alcohol, and also oligomeric glycosides with a degree of oligomerization up to preferably about 8 are suitable. The degree of oligomerization here is a statistical average value based on a homolog distribution customary for such technical products. Products which are available under the name Plantacare® or Plantaren® comprise a glucosidically bonded $C_8$-$C_{16}$-alkyl group on an oligoglucoside radical, the average degree of oligomerization of which is 1 to 2. The acylglucamides derived from glucamine are also suitable as nonionic emulsifiers. According to the invention, preference is given to a product which is sold under the name Emulgade® PL 68/50 by BASF Deutschland GmbH and is a 1:1 mixture of alkyl polyglucosides and fatty alcohols. According to the invention, it is advantageously also possible to use a mixture of lauryl glucoside, polyglyceryl-2 dipolyhydroxystearate, glycerol and water, which is commercially available under the name Eumulgin® VL 75.

Suitable emulsifiers are also substances such as lecithins and phospholipids. Examples of natural lecithins which may be mentioned are the kephalins, which are also referred to as phosphatidic acids and are derivatives of 1,2-diacyl-sn-glycerol-3-phosphoric acids. By contrast, phospholipids are usually understood as meaning mono- and preferably diesters of phosphoric acid with glycerol (glycerol phosphates) which are generally included with the fats. In addition, sphingosines and/or sphingolipids are also suitable.

Silicone emulsifiers, for example, may be present as emulsifiers. These can be selected for example from the group of alkylmethicone copolyols and/or alkyldimethicone copolyols, in particular from the group of compounds which are characterized by the following chemical structure:

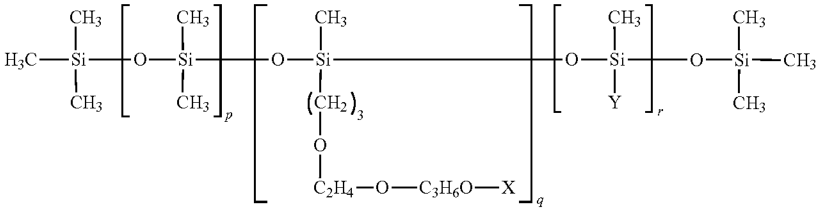

in which X and Y, independently of one another, are selected from the group H (hydrogen), and the branched and unbranched alkyl groups, acyl groups and alkoxy groups having 1-24 carbon atoms, p is a number from 0-200, q is a number from 1-40, and r is a number from 1-100.

One example of silicone emulsifiers to be used particularly advantageously within the context of the present invention are dimethicone copolyols, which are sold by Evonik Goldschmidt under the trade names AXIL® B 8842, ABIL® B 8843, ABIL® B 8847, ABIL® B 8851, ABIL® B 8852, ABIL® B 8863, ABIL® B 8873 and ABIL® B 88183.

A further example of interface-active substances to be used particularly advantageously within the context of the present invention is cetyl PEG/PPG-10/1 dimethicone (cetyl dimethicone copolyol), which is sold by Evonik Goldschmidt under the trade name ABIL® EM 90.

A further example of interface-active substances to be used particularly advantageously within the context of the present invention is the cyclomethiconedimethicone copolyol, which is sold by Evonik Goldschmidt under the trade name ABIL® EM 97 and ABIL® WE 09.

Furthermore, the emulsifier lauryl PEG/PPG-18/18 methicone (laurylmethicone copolyol) has proven to be very particularly advantageous and is available under the trade name Dow Corning® 5200 Formulation Aid from Dow Corning Ltd. Also advantageous is a silicone emulsifier with the INCI name Cyclopentasiloxane and PEG/PG-18-18 Dimethicone, which is available for example under the trade name Dow Corning® 5225 C Formulation Aid.

A further advantageous silicone emulsifier is octyl dimethicone ethoxyglucoside from Wacker. For a water-in-silicone oil emulsion according to the invention, all known emulsifiers used for this type of emulsion can be used. Water-in-silicone emulsifiers particularly preferred according to the invention here are cetyl PEG/PPG-10/1 dimethicone and lauryl PEG/PPG-18/18 methicone [e.g. ABIL® EM 90 Evonik Goldschmidt), DC5200 Formulation Aid (Dow Corning)], and any desired mixtures of both emulsifiers.

A suitable anionic O/W emulsifier is e.g. the product available under the INCI name Disodium Cetearyl Sulfosuccinate (trade name Eumulgin® Prisma, BASF GmbH).

Surfactants

In one embodiment of the invention, the preparations according to the invention comprise at least one surfactant as interface-active compounds. Interface-active substances which may be present are anionic, nonionic, cationic and/or amphoteric or zwitterionic surfactants. In surfactant-containing cosmetic preparations, such as, for example, shower gels, foam baths, shampoos etc., preferably at least one anionic surfactant is present.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucuronic acid derivatives, fatty acid N-alkylglucamides, protein hydrolyzates (in particular wheat-based plant products), polyol fatty acid esters, sugar esters, sorbitan esters, polysorbates and amine oxides. If the nonionic surfactants comprise polyglycol ether chains, these can have a conventional homolog distribution, but preferably have a narrowed homolog distribution.

Zwitterionic surfactants is the term used to refer to those surface-active compounds which carry at least one quaternary ammonium group and at least one —$COO^{(-)}$ or —$SO_3^{(-)}$ group in the molecule. Particularly suitable zwitterionic surfactants are the so-called betaines, such as the N-alkyl-N, N-dimethylammonium glycinates, for example cocoalkyldimethylammonium glycinate, N-acylaminopropyl-N,N-dimethylammonium glycinates, for example cocoacyl-aminopropyldimethylammonium glycinate, and 2-alkyl-3-carboxylmethyl-3-hydroxyethyl-imidazoline having in each case 8 to 18 carbon atoms in the alkyl or acyl group, and also cocoacylaminoethylhydroxyethyl carboxymethylglycinate. A preferred zwitterionic surfactant is the fatty acid amide derivative known under the INCI name Cocamidopropyl Betaine.

Likewise suitable, especially as co-surfactants, are ampholytic surfactants. Ampholytic surfactants are understood as meaning those surface-active compounds which, apart from a $C_8$-$C_{18}$-alkyl or acyl group in the molecule, comprise at least one free amino group and at least one —COOH or —SO H group and are capable of forming internal salts. Examples of suitable ampholytic surfactants are N-alkylglycines, N-alkylpropionic acids, N-alkylaminobutyric acids, N-alkyliminodipropionic acids (commercially available for example under the trade name Dehyton® DC), N-hydroxyethyl N-alkylamidopropylglycines, N-alkyltaurines, N-alklylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12-18}$-acylsarcosine. Also suitable are derivatives of N-alkyliminodipropionic acids, such as, for example, N-lauryl-beta-iminopropionates, commercially available under the trade name Deriphat® 160 C. Also suitable are amphoacetates, such as e.g. cocoamphoacetates (e.g. Dehyton® MC) or cocoamphodiacetates (e.g. Dehyton® DC).

Anionic surfactants are characterized by a water-solubilizing, anionic group such as e.g. a carboxylate, sulfate, sulfonate, citrate or phosphate group and a lipophilic radical. Skin-compatible anionic surfactants are known in large numbers to the person skilled in the art from relevant handbooks and are commercially available. These are in particular alkylsulfates in the form of their alkali metal, ammonium or alkanolammonium salts, alkyl ether sulfates, alkyl ether carboxylates, acyl isethionates, acyl sarcosinates, acyltaurines with linear alkyl or acyl groups having 12 to 18 carbon atoms, and sulfosuccinates and acylglutamates in the form of their alkali metal or ammonium salts. Particularly suitable anionic surfactants are glyceryl stearate Citrate (such as e.g. commercially available under the trade names Imwitor®370, Imwitor® 372P, Axol® C, 62 or Dracorin® CE 614035) or glycerol stearate lactate compounds. An example of a suitable alkylsulfate is sodium cetearyl sulfate (trade name Lanette® E), an example of a suitable phosphate is potassium cetyl phosphate (trade name Amphisol® K). An example of a suitable acylglutamate is sodium stearoyl glutamate (trade name e.g. Eumulgin® SG). A further example of a suitable anionic surfactant is sodium lauryl glucose carboxylate (trade name Plantapon® LGC).

Cationic surfactants which can be used are in particular quaternary ammonium compounds. Preference is given to ammonium halides, in particular chlorides and bromides, such as alkyltrimethylammonium chlorides, dialkyldimethylammonium chlorides and trialkylmethylammonium chlorides, e.g. cetyltrimethylammonium chloride, stearyltrimethyl-ammonium chloride, distearyldimethylammonium chloride, lauryldimethylammonium chloride, lauryldimethylbenzylammonium chloride and tricetylmethylammonium chloride. Suitable pseudo cationic surfactants are, for example, stearylaminopropyldimethylamine (commercially available under the trade name Dehyquart® S18 or Incromine® SB or TegoAmide® S18). Furthermore, the very readily biodegradable quaternary ester compounds, such as, for example, the dialkylammonium methosulfates and methylhydroxyalkyldialkoyl-oxyalkylammonium methosulfates sold under the trade name Stepantex® and the corresponding products of the Dehyquart® series, can be used as cationic surfactants. The term "esterquats" is generally understood as meaning quaternized fatty acid triethanolamine ester salts. They can impart a particular soft feel to the preparations according to the invention. These are known substances which are prepared by the relevant methods of organic chemistry. Further cationic surfactants which can be used according to the invention are the quaternized protein hydrolysates. Suitable cationic surfactants are, for example, Dipalmitoylethyl Hydroxyethylmonium Methosulfate (trade name Dehyquart® C4046), Distearoylethyl Hydroxyethylmonium Methosulfate (trade name Dehyquart® F75), Dicocoylethyl Hydroxyethylmonium Methosulfate (trade name Dehyquart® L80), Behentrimonium Chloride (trade name Varisoft® BT), Distearyldimonium Chloride (trade name Varisoft® TA 100), Palmitamidopropyltrimonium Chloride (trade name Varisoft® PATC).

Polymers

In one embodiment of the invention, the preparations according to the invention comprise at least one polymer. The preparations according to the invention comprise the polymer(s) in an amount of from 0 to 20% by weight, preferably 0.05 to 18% by weight, preferably 0.05 to 15% by weight, particularly preferably 0.05 to 10% by weight, in particular 0.1 to 1% by weight, based on the total weight of the preparations. In a preferred embodiment of the invention, the preparations according to the invention comprise the polymer/polymers in an amount of from 0.1 to 5% by weight, in particular 0.1 to 3% by weight, in particular 0.1 to 2% by weight, based on the total weight of the preparation.

Suitable cationic polymers are, for example, cationic cellulose derivatives, such as e.g. a quaternized hydroxyethylcellulose, which is available under the name Polymer JR 400® from Amerchol, cationic starch, copolymers of diallylammonium salts and acrylamides, quaternized vinylpyrrolidone/vinylimidazole polymers, such as e.g. Luviquat® (BASF), condensation products of polyglycols and amines, quaternized collagen polypeptides, such as, for example, lauryldimonium hydroxypropyl hydrolyzed collagen (Lamequat® L/Grünau), quaternized wheat polypeptides, polyethyleneimine, cationic silicone polymers, such as e.g. amidomethicones, copolymers of adipic acid and dimethylaminohydroxypropyldiethylene-triamine (Cartaretine®/Sandoz), copolymers of acrylic acid with dimethyldiallylammonium chloride (Merquat® 550/Chemviron), polyaminopolyamides, cationic chitin derivatives such as, for example, quaternized chitosan, optionally in microcrystalline distribution, condensation products of dihaloalkylene, such as e.g. dibromobutane with bisdialkylamines, such as e.g. bis-dimethylamino-1,3-propane, cationic guar gum, such as e.g. Jaguar® CBS, Jaguar® C-17, Jaguar C-16 from Celanese, quaternized ammonium salt polymers, such as e.g. Mirapol® A-15, Mirapol® AD-1, Mirapol® AZ-1 from Miranol.

Suitable anionic, zwitterionic, amphoteric and nonionic polymers are, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked and polyol-crosslinked polyacrylic acids, acrylamidopropyltrimethylammonium chloride/acrylate copolymers, octylacrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers, and optionally derivatized cellulose ethers and silicones.

Particularly suitable anionic polymers are those with the INCI name Carbomer, such as e.g. the Carbopol grades 980, 980, 981, 1382, 2984, 5984, and the products available under the trade names Rheocare® C plus and Rheocare®400. Furthermore suitable anionic polymers are those with the INCI name Acrylates/C10-30 Alkyl Acrylate Crosspolymer (trade name e.g. Pemulen® TR, Pemulen® TR 2, Carbopol® Ultrez), Acrylates Copolymer (trade name e.g. Rheocare TTA, TTN, TTN-2), Acrylamide/Sodium Acrylate Copolymer (trade name e.g. Cosmedia® ATC), Sodium Polyacrylate (trade name e.g. Cosmedia® ATH, Cosmedia® SP), Polyacrylamides (trade name e.g. Sepigel® 305 or Sepigel® 501). Preferred anionic polymers are polyacrylic acid homopolymers and copolymers.

Furthermore suitable polymers are silicone elastomer gums, such as e.g. silicone elastomer mixtures, such as e.g. mixtures with the INCI names Cyclopentasiloxane (and) Dimethiconol (and) Dimethicone Crosspolymer (trade name Dow Corning® DC 9027), mixtures with the INCI name Isodecyl Neopentanoate (and) Dimethicone/bis-isobutyl PPG-20 Crosspolymer (trade name Dow Corning® DC EL 8051 IN), mixtures with the INCI name Dimethicone/Vinyl Dimethicone Crosspolymer (and) C12-14 Pareth-12) (trade name Dow Corning® DC 9509), and mixtures with the INCI name Dimethicone/Vinyl Dimethicone Crosspolymer (and) Silica (trade name Dow Corning® DC 9701 Cosmetic Powder).

Suitable polymers are likewise polysaccharides, in particular xanthan gum, guar gum, agar agar, alginates and tyloses, and also tara gum, carrageenan, sclerotium gum and natural cellulose.

Further Oil Components

Bodycare compositions, such as creams, body oils, lotions and milks, usually comprise a series of oil components and emollients which contribute to further optimizing the sensory properties. The inventive polyol ester mixture can be used as the only oil component in the cosmetic or pharmaceutical composition, but can as well be mixed with further oil components.

Suitable further oil components are, for example, Guerbet alcohols based on fatty alcohols having 6 to 18, preferably 8 to 10, carbon atoms, and also esters such as myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of $C_{18}$-$C_{38}$-alkylhydroxycarboxylic acids with linear or branched $C_6$-$C_{22}$-fatty alcohols, in particular dioctyl malate, esters of linear and/or branched fatty acids with polyhydric alcohols (such as e.g. propylene glycol, dimerdiol or trimertriol), triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with polyols having 2 to 10 carbon atoms and 2 to 6 hydroxyl groups, plant oils, branched primary alcohols, substituted cyclohexanes, linear and branched $C_6$-$C_{22}$-fatty alcohol carbonates, such as e.g. Dicaprylyl Carbonate (Cetiol® CC), Guerbet carbonates based on fatty alcohols having 6 to 18, preferably 8 to 10 carbon atoms, esters of benzoic acid with linear and/or branched $C_6$-$C_{22}$-alcohols (e.g. Finsolv TN), linear or branched, symmetrical or asymmetrical dialkyl ethers having 6 to 22 carbon atoms per alkyl group, such as e.g. dicaprylyl ether (Cetiol® OE), ring-opening products of epoxidized fatty acid esters with polyols and hydrocarbons or mixtures thereof. Also suitable are esters of 2-propylheptanol with n-octanoic acid, such as e.g. commercially available under the trade name Cetiol® Sensoft (BASF GmbH). Also suitable are hydrocarbons, such as for example undecane and/or tridecane. Also suitable are alkanes, such as e.g. the mixtures with the INCI name Coconut/Palm/Palm Kernel Oil Alkanes (trade name Vegelight 1214 from Biosynthesis).

Fats and waxes are encompassed by oil components. Fats are understood as meaning triacylglycerols, i.e. the triple esters of fatty acids with glycerol. Preferably, they comprise saturated, unsaturated and unsubstituted fatty acid radicals. These may also be mixed esters, i.e. triple esters of glycerol with various fatty acids. So-called hydrogenated fats and oils which are obtained by partial hydrogenation can be used as consistency regulators if necessary. Plant hydrogenated fats and oils are preferred, e.g. hydrogenated castor oil, peanut oil, soya oil, rapeseed oil, colza seed oil, cotton seed oil, soya oil, sunflower oil, palm oil, palm kernel oil, linseed oil, almond oil, corn oil, olive oil, sesame oil, cocoa butter, shea butter and coconut fat.

The triple esters of glycerol with C12-C60-fatty acids and in particular C12-C36-fatty acids are inter alia suitable. These include hydrogenated castor oil, a triple ester of glycerol and a hydroxystearic acid, which is commercially available for example under the name Cutina HR. Likewise suitable are glycerol tristearate, glycerol tribehenate (e.g. Syncrowax HRC), glycerol tripalmitate or the triglyceride mixtures known under the name Syncrowax HGLC, with the proviso that the melting point of the wax component or of the mixture is 30° C. or above.

According to the invention, in particular mono- and diglycerides or mixtures of these partial glycerides can be used as wax components. The glyceride mixtures which can be used according to the invention include the products Novata AB and Novata B (mixture of C12-C18-mono-, di- and triglycerides) and also Cutina® HVG (Hydrogenated Vegetable Glycerides) or Cutina® GMS (glyceryl stearate) marketed by BASF.

The fatty alcohols which can be used according to the invention as consistency agent include the C12-C50-fatty alcohols. The fatty alcohols can be obtained from natural fats, oils and waxes, such as, for example, myristyl alcohol, 1-pentadecanol, cetyl alcohol, 1-hepta-decanol, stearyl alcohol, 1-nonadecanol, arachidyl alcohol, 1-heneicosanol, behenyl alcohol, brassidyl alcohol, lignoceryl alcohol, ceryl alcohol or myricyl alcohol. According to the invention, preference is given to saturated unbranched fatty alcohols. However, unsaturated, branched or unbranched fatty alcohols can also be used according to the invention as wax component provided they have the required melting point. According to the invention, it is also possible to use fatty alcohol segments, as are produced during the reduction of naturally occurring fats and oils such as e.g. beef tallow, peanut oil, coltsa oil, cotton oil, soya oil, sunflower oil, palm kernel oil, linseed oil, castor oil, corn oil, rapeseed oil, sesame oil, cocoa butter and cocoa fat. However, it is also possible to use synthetic alcohols, e.g. the linear, even-numbered fatty alcohols of the Ziegler synthesis (alfols) or the sometimes branched alcohols from the oxo synthesis (dobanols). According to the invention, C14-C22-fatty alcohols are particularly preferably suitable, which are marketed for example by BASF under the name Lanette 16 (C16-alcohol), Lanette 14 (C14-alcohol), Lanette O (C16/C18-alcohol) and Lanette 22 (C18/C22-alcohol). Fatty alcohols give the preparations a drier skin feel than triglycerides and are therefore preferred over the latter.

Wax components which can be used are also C14-C40-fatty acids or mixtures thereof. These include, for example, myristic acid, pentadecanoic acid, palmitic acid, margaric acid, stearic acid, nonadecanoic acid, arachic acid, behenic acid, lignoceric acid, cerotic acid, melissic acid, erucic acid and elaeostearic acid, and also substituted fatty acids, such as e.g. 12-hydroxystearic acid, and the amides or monoethanolamides of the fatty acids, this list being exemplary and non-limiting in character.

It is possible to use for example natural plant waxes, such as candelilla wax, carnauba wax, japan wax, esparto grass wax, cork wax, guaruma wax, ricegerm oil wax, sugarcane wax, ouricury wax, montan wax, sunflower wax, fruit waxes such as orange waxes, lemon waxes, grapefruit wax, bayberry wax and animal waxes, such as e.g. beeswax, schellack wax, spermaceti, wool wax and uropygial grease. Within the context of the invention, it may be advantageous to use hydrogenated waxes. The natural waxes which can be used according to the invention also include the mineral waxes, such as e.g. ceresin and ozokerite or the petrochemical waxes, such as e.g. petrolatum, paraffin waxes and microwaxes. Wax components which can be used are also chemically modified waxes, in particular the hard waxes, such as e.g. montan ester waxes, sasol waxes and hydrogenated jojoba waxes. The synthetic waxes which can be used according to the invention include, for example, wax-like polyalkylene waxes and polyethylene glycol waxes. Plant waxes are preferred according to the invention.

The wax component can likewise be selected from the group of wax esters of saturated and/or unsaturated, branched and/or unbranched alkanecarboxylic acids and saturated and/or unsaturated, branched and/or unbranched alcohols, from the group of esters of aromatic carboxylic acids, dicarboxylic acids, tricarboxylic acids and hydroxycarboxylic acids (e.g. 12-hydroxystearic acid) and saturated and/or unsaturated, branched and/or unbranched alcohols, and also from the group of the lactides of long-chain hydroxycarboxylic acids. Examples of such esters are the C16-C40-alkyl stearates, C20-C40-alkyl stearates (e.g. Kesterwachs K82H), C20-C40-dialkyl esters of dimer acids, C18-C38-alkyl hydroxystearoylstearates or C20-C40-alkyl erucates. It is also possible to use C30-C50-alkyl beeswax, tristearyl citrate, triisostearyl citrate, stearyl heptanoate, stearyl octanoate, trilauryl citrate, ethylene glycol dipalmitate, ethylene glycol distearate, ethylene glycol di(12-hydroxystearate), stearyl stearate, palmityl stearate, stearyl behenate, cetyl ester, cetearyl behenate and behenyl behenate.

UV-Filter

Another subject matter of the invention relates to preparations comprising at least one compound according to claim 1 and at least one UV photoprotective filter, preferably an oil-soluble UV photoprotective filter.

According to the invention, suitable UV photoprotective filters are organic substances (photoprotective filters) that are liquid or crystalline at room temperature and which are able to absorb ultraviolet radiation and release the absorbed energy again in the form of longer-wave radiation, e.g. heat. UV filters can be oil-soluble or water-soluble. Typical oil-soluble UV-B filters or broad spectrum UV A/B filters to be mentioned are e.g.:

3-benzylidenecamphor or 3-benzylidenenorcamphor (Mexoryl SDS 20) and derivatives thereof, e.g. 3-(4-methylbenzylidene)camphor, as described in EP 0693471 B1

3-(4'-trimethylammonium)benzylidenebornan-2-one methylsulfate (Mexoryl SO)

3,3'-(1,4-phenylenedimethine)bis(7,7-dimethyl-2-oxobicyclo[2.2.1]heptane-1-methanesulfonic acid) and salts (Mexoryl SX)

3-(4'-sulfo)benzylidenebornan-2-one and salts (Mexoryl SL) polymer of N-{(2 and 4)-[2-oxoborn-3-ylidene) methyl}benzyl]acrylamide (Mexoryl SW)

2-(2H-benzotriazol-2-yl)-4-methyl-6-(2-methyl-3-(1,3,3,3-tetramethyl-1-(trimethylsilyloxy)disiloxanyl)propyl) phenol (Mexoryl SL)

4-aminobenzoic acid derivatives, preferably 2-ethylhexyl 4-(dimethylamino)benzoate, 2-octyl 4-(dimethylamino)benzoate and amyl 4-(dimethylamino)benzoate;

esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomenthyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl 4-methoxybenzmalonate;

triazine derivatives, such as e.g. 2,4,6-trianilino(p-carbo-2'-ethyl-1'-hexyloxy)-1,3,5-triazine and 2,4,6-tris[p-(2-ethylhexyloxycarbonyl)anilino]-1,3,5-triazine (Uvinul T 150) as described in EP 0818450 A1 or bis(2-ethylhexyl) 4,4'-[(6-[4-((1,1-dimethylethyl)aminocarbonyl)phenylamino]-1,3,5-triazine-2,4-diyl)diimino] bisbenzoate (Uvasorb® HEB);

2,2-(methylenebis(6-(2H-benzotriazol-2-yl)-4-(1,1,3,3-tetramethylbutyl)phenol) (Tinosorb M);

2,4-bis[4-(2-ethylhexyloxy)-2-hydroxyphenyl]-6-(4-methoxyphenyl)-1,3,5-triazine (Tinosorb S);

propane-1,3-diones, such as e.g. 1-(4-tert-butylphenyl)-3-(4'-methoxyphenyl)propane-1,3-dione;

ketotricyclo(5.2.1.0)decane derivatives, as described in EP 0694521 B1;

dimethicodiethylbenzalmalonates (Parsol SLX).

Suitable water-soluble UV filters are:

2-phenylbenzimidazole-5-sulfonic acid and the alkali metal, alkaline earth metal, ammonium, alkyl ammonium, alkanol ammonium and glucammonium salts thereof;

2,2-((1,4-phenylene)bis(1H-benzimidazole-4,6-disulfonic acid, monosodium salt) (Neo Heliopan AP)

sulfonic acid derivatives of benzophenones, preferably 2-hydroxy-4-methoxybenzophenone-5-sulfonic acid and its salts;

sulfonic acid derivatives of 3-benzylidenecamphor, such as e.g. 4-(2-oxo-3-bornylidenemethyl)benzenesulfonic acid and 2-methyl-5-(2-oxo-3-bornylidene)sulfonic acid and salts thereof.

In a preferred embodiment of the invention, the preparations comprise at least one oil-soluble UV photoprotective filter and at least one water-soluble UV photoprotective filter.

Suitable typical UV-A filters are in particular derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol® 1789), 1-phenyl-3-(4'-isopropylphenyl)propane-1,3-dione, and also enamine compounds, as described in DE 19712033 A1 (BASF), and also benzoic acid, 2-[4-(diethylamino)-2-hydroxybenzoyl]-, Hexyl Ester (Uvinul® A plus).

The UV-A and UV-B filters can of course also be used in mixtures. Particularly favorable combinations consist of the derivatives of benzoylmethane, e.g. 4-tert-butyl-4'-methoxydibenzoylmethane (Parsol® 1789) and 2-ethylhexyl 2-cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Combinations of this type are advantageously combined with water-soluble filters such as e.g. 2-phenylbenzimidazole-5-sulfonic acid and the alkali metal, alkaline earth metal, ammonium, alkyl ammonium, alkanol ammonium and glucammonium salts thereof.

The preparations according to the invention can also comprise insoluble photoprotective pigments, namely finely disperse metal oxides and/or salts. Examples of suitable metal oxides are in particular zinc oxide and titanium dioxide and also oxides of iron, zirconium, silicon, manganese, aluminum and cerium, and mixtures thereof. Salts which can be used are silicates (talc), barium sulfate or zinc stearate. The oxides and salts are used in the form of the pigments for skincare and skin-protecting emulsions and also for decorative cosmetics. The particles should have an average diameter of less than 100 nm, preferably between 5 and 50 nm and in particular between 15 and 30 nm. They can have a spherical form, although it is also possible to use particles which have an ellipsoidal form or a form which deviates in some other way from the spherical shape. The pigments can also be present in surface-treated form, i.e. hydrophilicized or hydrophobicized. Typical examples thereof are coated titanium dioxides, such as e.g. titanium dioxide T 805 (Degussa) or Eusolex® T, Eusolex® T-2000, Eusolex® T-Aqua, Eusolex® AVO, Eusolex® T-ECO, Eusolex® T-OLEO and Eusolex® T-S(Merck). Typical examples thereof are zinc oxides, such as e.g. zinc oxide neutral, zinc oxide NDM (Symrise) or Z-Cote® (BASF) or SUNZnO-AS and SUNZnO-NAS (Sunjun Chemical Co. Ltd.). Suitable hydrophobic coatings here are primarily silicones and specifically trialkoxyoctylsilanes or simethicones. In sunscreen compositions, preference is given to using so-called micropigments or nanopigments. Preferably, micronized zinc oxide is used.

As well as the two aforementioned groups of primary photoprotective substances, it is also possible to use secondary photoprotective agents of the antioxidant type, which interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides such as D,L-carnosine, D-carnosine, L-carnosine and derivatives thereof (e.g. anserine), carotenoids, carotenes (e.g. -carotene, -carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides, nucleosides and salts), and also sulfoximine compounds (e.g. buthionine sulfoximines, homocysteine sulfoximine, buthionine sulfones, penta-, hexa-, heptathionine sulfoximine) in very low tolerated doses (e.g. pmol to mol/kg), also (metal) chelating agents (e.g. α-hydroxy fatty acids, palmitic acid, phytic acid, lactoferrin), α-hydroxy acids (e.g. citric acid, lactic acid, maleic acid), humic acid, bile acid, bile extracts, bilirubin, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO4), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) suitable according to the invention of these specified active ingredients.

In a preferred embodiment of the invention, the preparations comprise at least one UV photoprotective filter selected from the group consisting of 4-methylbenzylidenecamphor, benzophenone-3, butylmethoxydibenzoyl methane, bis-ethylhexyloxyphenol methoxyphenyl triazine, methylene bis-benzotriazolyl tetramethylbutylphenol, diethylhexyl butamidotriazone, ethylhexyl triazone and diethylamino hydroxybenzoyl hexyl benzoate, 3-(4'-trimethylammonium)benzylidenebornan-2-one methylsulfate, 3,3'-(1,4-phenylene-dimethine)bis(7,7-dimethyl-2-oxobicyclo[2.2.1]heptane-1-methanesulfonic acid) and its salts, 3-(4'sulfo)benzylidenebornan-2-one and its salts, polymer of N-{(2 and 4)-[2-oxoborn-3-ylidene)methyl}benzyl]acrylamide, 2-(2H-benzotriazol-2-yl)-4-methyl-6-(2-methyl-3-(1,3,3,3-tetramethyl-1-(trimethylsilyloxy)disiloxanyl)propyl)phenol, dimethicodiethyl benzalmalonate and their mixtures.

These UV photoprotective filters are commercially available, for example, under the following trade names:

NeoHeliopan® MBC (INCI: 4-methylbenzylidene camphor; manufacturer: Symrise); NeoHeliopan® BB (INCI: benzophenone-3, manufacturer: Symrise); Parsol® 1789 (INCI: butyl methoxydibenzoylmethane, manufacturer: Hoffmann La Roche (Givaudan); Tinosorb® S (INCI: bis-ethylhexyloxyphenol methoxyphenyl triazine); Tinosorb® M (INCI: methylene bis-benzotriazolyl tetramethylbutylphenol): manufacturer: Ciba Specialty Chemicals Corporation; Uvasorb® HEB (INCI: diethylhexyl butamidotriazone, manufacturer: 3V Inc.), Unvinul® T 150 (INCI: ethylhexyl triazone, manufacturer: BASF AG); Uvinul® A plus (INCI: diethylamino hydroxybenzoyl hexyl benzoate: manufacturer: BASF AG; Mexoryl® SO: 3-(4'-trimethylammonium)benzylidenebornan-2-one methylsulfate, INCI: camphor benzalkonium methosulfate; Mexoryl® SX: 3,3'-(1,4-phenylenedimethine)bis(7,7-dimethyl-2-oxobicyclo[2.2.1]heptane-1-methanesulfonic acid), CTFA: INCI terephthalylidene dicamphor sulfonic acid; Mexory® SL: 3-(4'-sulfo)benzylidenebornan-2-one, INCI benzylidene camphor sulfonic acid; Mexoryl® SW: polymer of N-{(2 and 4)-[2-oxoborn-3-ylidene)methyl}benzyl]acrylamide, INCI polyacrylamidomethyl benzylidene camphor; Mexoryl® SL: 2-(2H-benzotriazol-2-yl)-4-methyl-6-(2-methyl-3-(1,3,3,3-tetramethyl-1-(trimethylsilyloxy)disiloxanyl)propyl)phenol; INCI: DROMETRIZOLE TRISILOXANE; Parsol® SLX: dimethicodiethylbenzalmalonate, INCI polysilicone-15.

The preparations according to the invention can comprise the UV photoprotective filters in amounts of from 0.5 to 30% by weight, preferably 2.5 to 20% by weight, particularly preferably 5-15% by weight-based on the preparation.

Further Ingredients

Suitable thickeners are, for example, Aerosil grades (hydrophilic silicas), carboxymethylcellulose and hydroxyethyl- and hydroxypropylcellulose, polyvinyl alcohol, polyvinylpyrrolidone and bentonite such as e.g. Bentone® Gel VS-5PC (Rheox). A suitable thickener is for example the product with the INCI name Dicaprylyl Carbonate, Stearalkonium Hectorite and Propylene Carbonate available under the trade names Cosmedia® Gel CC. Biogenic active ingredients are to be understood as meaning, for example, tocopherol, tocopherol acetate, tocopherol palmitate, ascorbic acid, (deoxy)ribonucleic acid and a fragmentation product thereof, β-glucans, retinol, bisabolol, allantoin, phytantriol, panthenol, AHA acids, amino acids, ceramides, pseudoceramides, essential oils, plant extracts, such as e.g. prune extract, bambara nut extract and vitamin complexes. Deodorizing active ingredients/antiperspirants counteract, mask or eliminate body odors. Body odors are formed as a result of the action of skin bacteria on apocrine perspiration, during which unpleasant smelling degradation products are formed. Accordingly, antimicrobial agents, enzyme inhibitors, odor absorbers or odor maskers, inter alia, are suitable as deodorizing active ingredients. Suitable insect repellents are, for example, N,N-diethyl-m-toluamide, 1,2-pentanediol or ethyl 3-(N-n-butyl-N-acetylamino)propionate), which is sold under the name Insect Repellent® 3535 by Merck KGaA, and also butylacetylaminopropionate. A suitable self-tanning agent is dihydroxyacetone or erythrulose. Suitable tyrosine inhibitors, which prevent the formation of melanin and are used in depigmentation compositions, are, for example, arbutin, ferulic acid, kojic acid, cumaric acid and ascorbic acid (vitamin C). Suitable preservatives are, for example, phenoxyethanol, formaldehyde solutions, parabens, pentanediol, chlorphenesin, caprylyl glycol, ethylhexylglycerols or sorbic acid, and also the silver complexes known under the name Surfacine® and the other substance classes listed in annex 6, part A and B of the Cosmetics Ordinance. Perfume oils which may be mentioned are mixtures of natural and synthetic fragrances. Natural fragrances are extracts from flowers, stems and leaves, fruits, fruit peels, roots, woods, herbs and grasses, needles and branches, resins and balsams. Also suitable are animal raw materials, such as, for example, civet and castoreum, and also synthetic fragrance compounds of the ester, ether, aldehyde, ketone, alcohol and hydrocarbon types. Suitable pearlescent waxes or pearlescent compounds, particularly for use in surface-active formulations, are, for example: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have in total at least 24 carbon atoms, specifically laurone and distearyl ether; stearyl citrate, cyclodextrin, fatty acids such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Superfatting agents which can be used are substances such as, for example, lanolin and lecithin, and also polyethoxylated or acylated lanolin and lecithin derivatives, polyol fatty acid esters, monoglycerides and fatty acid alkanolamides, the latter simultaneously serving as foam stabilizers. A suitable superfatting agent is, for example, the mixture of cocoglucosides and glyceryl oleate (commercially available as Lamesoft® PO65 from BASF).

Suitable fillers are substances which, for example, improve the sensory or cosmetic properties of a preparation and which, for example, produce or boost a velvety or silky feel (so-called skin sensory modifier). Suitable fillers are starch and starch derivatives (such as e.g. tapioca starch, aluminum starch octenyl succinate, sodium octenyl succinate, distarch phosphate), pigments which do not serve primarily as UV filters or dyes (such as e.g. boron nitride) and/or Aerosil® (CAS No. 7631-86-9), and/or talc, and also for example polymethyl methacrylate (e.g. Cosmedia® PMMA V8/V12), silica (e.g. Cosmedia® SILC), stearalkonium hectorite (as present in the commercially available product Cosmedia® Gel CC), and also HDI/trimethylol hexyllactone crosspolymer (as present in the commercially available product Cosmedia® CUSHION).

Stabilizers which can be used are metal salts of fatty acids, such as e.g. magnesium, aluminum and/or zinc stearate or ricinoleate. To improve the flow behavior, also hydrotropes, such as, for example, ethanol isopropyl alcohol, or polyols, can be used. Polyols which are suitable here have preferably 2 to 15 carbon atoms and at least two hydroxyl groups. The polyols can also contain further functional groups, in particular amino groups, and/or be modified with nitrogen.

The polyolester according to claim 1 is as well suitable in cosmetic and/or pharmaceutical preparations for the impregnation or coating of utility wipes and hygiene wipes which are used for caring and cleaning the body and/or for bodycare.

Utility wipes and hygiene wipes which may be mentioned by way of example are: tissues, papers, wipes, nonwoven products, sponges, puffs, plasters and bandages which are used in the field of hygiene and care. These may be wet wipes for baby hygiene and babycare, cleansing wipes, face cleansing wipes, skincare wipes, care wipes with active ingredients to combat skin aging, wipes with sunscreen formulations and insect repellents, and also wipes for decorative cosmetics or for after-sun treatment, toilet wet wipes, antiperspirant wipes, diapers, pocket tissues, wet wipes, hygiene products, and self-tanning wipes.

EXAMPLES

(1) Preparation Examples 1.1 Inventive Polyol Ester Mixture Sample (INV):

230.3 g (2.5 mol) glycerin, 460.3 (2.1 mol) Palmera B1231 (C8+C10 FA: max. 1.5%, C12-FA: 50-62%, C14-FA: 15-26%, C16-FA: 8-14%, C18-FA: 7-14%, C18:1-FAS: max. 1%) and 244.4 g (0.9 mol) Fatty Acid L25MGS (FA<C14: max. 1%-C14-FA: 0-5%-C16-FA: 40.0-49.0%-C18-FA: 50.0-58.0%-FA>C18: max. 2%) (final distribution of fatty acids-see table 1)) were charged to a round bottomed flask with a propeller stirrer, side-arm water condenser and collection flask, nitrogen sparge thermometer (thermocouple) and isomantle, melted at 80° C. and gassed with nitrogen. 303.4 (1.5 mol) sebacic acid were added and the mixture was heated to 220° C. under nitrogen sparge removing water of reaction through the condenser. The reaction was stopped when an acid value of less than 2 mg KOH/g was reached (after 32 hrs) and the product discharged.

TABLE 2

Distribution of Fatty Acids of Inventive Polyolester found by GC analysis of the reaction product after alkaline saponification

| | wt % by GC after alkaline saponification |
|---|---|
| Sum fatty acids (FA) used | 100.0 |
| C8 and C10 FA | 0.5 |
| C12 FA | 36.6 |
| C14 FA | 13.6 |
| C16 FA | 22.6 |
| C18 FA | 25.6 |
| C18:1 FA | 0.3 |
| >C18 FA | 0.0 |

1.2 Comparison—Example with Behenic Acid (A)

184.2 g (2 mol) glycerin, 816.24 (2.4 mol) behenic acid (C22-85, Source: Cremer Oleo Division (≤C18-FA: <5%, C20-FA: ≤12%, C22-FA: 87.1%, >C22-FA: 1.8%) were charged to a three-necked flask with a propeller stirrer, 242.7 (1.2 mol) sebacic acid were added and the mixture was melted at 80° C. and gassed with nitrogen. Slowly the mixture was heated under stirring to 210° C. with nitrogen sparge removing water of reaction through the condenser. The reaction was stopped when an acid value of less than 2 mg KOH/g was reached (after 23 hrs) and the product discharged.

1.3 Comparison—Example with Different Fatty Acid Distribution (B)

231.1 g (2.5 mol) glycerol, 72.37 g caprylic (octanoic) acid (0.5 mol) (Edenor C8-98/100 Source: Emery (C6-FA: ≤1%, C8-FA: ≥99%, C10-FA: ≤1%)), 343.79 g (1.5 mol) myristic acid (tetradecanoic) (Edenor C14-98/100 Source: Emery (C12-FA: ≤1%, C14-FA:≥99%, C16-FA: ≤1%),) and 285.5 (1.0 mol) stearic (octadecanoic) acid (Edenor C818-98/100 Source: Emery (C16-FA: ≤2%, C8-FA: ≥99%, C18-FA: ≤2%)) were charged to a three-necked bottomed flask with a propeller stirrer, 304.4 g (1.5 mol) sebacic acid were added, the mixture was melted at 80° C. and gassed with nitrogen. Slowly this mixture was heated under stirring to 220° C. under nitrogen sparge removing water of reaction through the condenser. The reaction was stopped when an acid value of less than 2 mg KOH/g was reached (after 26.5 hrs) and the product discharged.

TABLE 3

Physico-chemical properties of two polyol ester mixtures according to example 1:

| | unit | pilot batch INV Batch 1 | pilot batch INV Batch 2 | method |
|---|---|---|---|---|
| acid value | mgKOH/g | 1.75 | 1.8 | ISO 660 |
| hydroxyl value | mgKOH/g | 74.8 | 74.7 | ISO 4326 |
| saponification value | mgKOH/g | 299.2 | 304.1 | ISO 3657 |
| water | % | <0.1 | <0.1 | ISO 4317 (KF) |
| colour, 40° C. | apha | 87 | | ISO6271 |
| density, 40° C. | g/ml | 0.9637 | 0.9645 | DIN 51757-D Ph. Eur. |

No changes in colour, odour or physical appearance after 11 months of storage at room temperature

(2) Sensoric Assessment—In Vivo Study

After toxicological clearance a sensory assessment was conducted to evaluate the sensory differences between the inventive polyol ester mixture and comparison B. The sample of comparison A was a solid waxy component which could not be distributed on the skin at room temperature, so that the inventive polyol ester mixture was investigated against a state of the art product (comparison B) as reference.

For the evaluation of the sensory assessment during application of the products the formulations were investigated by 11 volunteers of the trained panel in a direct comparison. The formulations were assessed with the fingers on forearms during absorption.

The grading is done on a five-point-scale from minus one to plus one, i.e. compared to the reference. The test is performed in a doubleblind mode. The samples are coded and applied randomly.

The eleven panelists evaluated the products individually answering the following parameters:

Pick up
Consistency
Distribution
Melting during distribution
Softness during distribution
Skin care effects during distribution
Waxiness during distribution
Stickiness during distribution
Gliding during distribution
Acceptance after distribution
Absorption after 1 min
Absorption after 3 min Both parameters, "pick-up" and "consistency", are assessed in a cream jar with the index finger.

For all other parameters, a measured amount (150 μl) of cream was put on the inside of each forearm and distributed there in 20 circles.

The sensory assessment takes place in an air-conditioned room at a temperature of 22° C. and a relative humidity of 40%. This climate-controlled room is equipped with HEPA-filters. It could be seen in table 3 that compared to the state of the art sample B—the inventive polyolester is easier to pick up with a softer consistency and leaves an improved impression regarding softness, waxiness and gliding during distribution.

TABLE 4

| Sensory assessment (n = 11) | | | | |
|---|---|---|---|---|
| | − | Standard | + | |
| Pick-up (difficult) | | | +++++++++++ | Pick-up (easy) |
| Consistency (hard) | | | +++++++++++ | Consistency (soft) |
| Distribution (difficult) | +++ | ++++ | ++++ | Distribution (easy) |
| Melting on skin (slow) | ++++++ | | +++++ | Melting on skin (fast) |
| Softness during distribution (less) | +++ | ++ | ++++++ | Softness during distribution (more) |
| Skin care effects during distribution (less) | ++ | +++++++ | ++ | Skin care effects during distribution (more) |
| Waxiness during distribution (more) | + | ++++ | ++++++ | Waxiness during distribution (less) |
| Stickiness during distribution (more) | + | +++++++++ | + | Stickiness during distribution (less) |
| Gliding during distribution (less) | ++ | +++ | ++++++ | Gliding during distribution (more) |
| Acceptance after distribution (little) | +++ | ++++ | ++++ | Acceptance after distribution (much) |
| Absorption I after 1 Minute (slow) | | ++++++++ | +++ | Absorption I after 1 Minute (fast) |
| Absorption II after 3 Minutes (slow) | | +++++++ | ++++ | Absorption II after 3 Minutes (fast) |

(3) Formulation Examples 5.1 Face Fluid

| | Ingredient | INCI | Inventive (with polyol ester mixture) Wt % | Comparison (with petrolatum) Wt % |
|---|---|---|---|---|
| A | Eumulgin SG | Sodium Stearoyl Glutamate | 0.40 | 0.40 |
| | Cutina GMS V | Glyceryl Stearate | 3.00 | 3.00 |
| | Lanette O | Cetearyl alcohol | 0.70 | 0.70 |
| | Myritol 331 | Cocoglycerides | 2.00 | 2.00 |
| | Cetiol PGL | Hexyldecyllaurate and Hexyldecanol | 4.00 | 4.00 |
| | Cetiol C5C | Coco-Caprylate/Caprate | 5.00 | 5.00 |
| | Cetiol Greentouch | According to example 1 | 5.00 | |
| | Vasiline Unilever pure | | | 5.00 |
| B | Water | | 74.45 | 74.45 |
| | Glycerin (Henkel) | | 3.00 | 3.00 |
| | Rheocare XGN | Xanthan Gum | 1.00 | 1.00 |
| C | NaBenzoat | | 0.55 | 0.55 |
| | Coviox T90 EU C | Tocopherol | 0.10 | 0.10 |
| | Perfume Cotton Touch | | 0.80 | 0.80 |
| D | Citric Acide 50% | pH-adjustment | q.s. | q.s. |
| | Viscosity (day 1) [mPas] Brookfield RVF, Sp 5, 10 rpm | | 15120 | 19320 |
| | Viscosity (week 1) [mPas] Brookfield RVF, Sp 5, 10 rpm | | ca. 15000 | ca. 20000 |

Preparation Advice:

Preparation of Phase B (Water, Glycerin Xanthan Gum):

Disperse xanthan gum into glycerin and add this premix into water under stirring.

Separately heat phases A (oil phase) and B to 75° C.

When the 2 phases are homogeneous, add phase A into phase B, and have a high stir for 10 minutes. Allow the emulsion to cool down while stirring.

At a temperature of T<40° C., add preservative, tocopherol and perfume and cool down to room temperature.

Adjust pH at 5.8-6.2 with citric acid.

5.2 Face Cream

| | Ingredient | INCI | Inventive (with polyol ester mixture) wt % | Comparison (with petrolatum) wt % |
|---|---|---|---|---|
| A | Cutina GMS-SE | | 5.50 | 5.50 |
| | Cutina FS 45 | Stearic Acid, Palmitic Acid | 1.00 | 1.00 |
| | Lanette O | Cetearyl alcohol | 3.00 | 3.00 |
| | Cetiol RLF | Caprylyl Caprylate/ Caprate | 8.00 | 8.00 |
| | Cegesoft PS6 | Olus Oil, Vegetable Oil | 6.00 | 6.00 |
| | Coviox T90 EU C | Tocopherol | 0.50 | 0.50 |
| | Cetiol Greentouch | According to example 1 | 7.00 | |
| | Vasiline Unilever pure | | | 7.00 |
| B | Glycerin | | 5.00 | 5.00 |
| | Water demin. | | 62.10 | 62.10 |
| | Rheocare XGN | Xanthan Gum | 0.20 | 0.20 |

-continued

| | Ingredient | INCI | Inventive (with polyol ester mixture) wt % | Comparison (with petrolatum) wt % |
|---|---|---|---|---|
| C | Perfume Cotton Touch | | 0.20 | 0.20 |
| | Preservative | | | |
| | Euxyl 9010 | Phenoxyethanol, Ethylhexylglycerin | 1.10 | 1.10 |
| | Sensiva SC 50 | Ethylhexylglycerin | 0.40 | 0.40 |
| D | Citronensäure 50% | pH-adjustment | qs | qs |
| | Viscosity (day 1) [mPas] Brookfield RVF, Sp 5, 10r pm | | 220,000-250,000 | 211,000-230,000 |
| | Viscosity (week 1) [mPas] Brookfield RVF, Sp 5, 10 rpm | | ca. 250,000 | ca. 250,000 |

Preparation Advice:

Preparation of Phase B (Water, Glycerin Xanthan Gum):

Disperse xanthan gum into glycerin and add this premix into water under stirring.

Separately heat phases A (oil phase) and B to 80° C.

When the 2 phases are homogeneous, add phase B into phase A, and allow the emulsion to cool down while stirring. Homogenize with a suitable dispersion unit (e.g. Ultra Turrax) at approximately 50° C. At a temperature below 40° C., add preservative and perfume and cool down to room temperature. Adjust pH at 5.8-6.5 with citric acid.

5.3 Lip Wax

| Ingredient | INCI | Inventive (with polyol ester mixture) wt % | Comparison (with petrolatum) % wt % |
|---|---|---|---|
| Cegesoft HF 62 | Hydrogenated vegetable oil | 10.00 | 10.00 |
| Cegesoft SH | Shorea Stenoptera Seed Butter | 5.00 | 5.00 |
| Myritol 318 | | 5.00 | 5.00 |
| Beeswax (Kahl) | | 5.00 | 5.00 |
| Carnauba wax (Kahl) | | 5.00 | 5.00 |
| Covi-ox T 70 C | tocopherol | 1.00 | 1.00 |
| Cetiol Greentouch | According to example 1 | 69.00 | |
| Vasiline Unilever pure | | | 69.00 |
| Parfüm Cotton Touch | perfume | q.s. | q.s. |

Preparation Advice:

Heat and melt all ingredients-besides tocopherol and perfume—at 85° C. while stirring. Cool down, add perfume and tocopherol at a temperature below 45° C. and fill in respective forms for further cooling to 20° C.

The invention claimed is:

1. A polyol ester obtained by an esterification reaction of a) 0.8 to 1.2 mol glycerol b) 0.5 to 0.7 mol sebacic acid c) 1.0 to 1.4 mol of a monocarboxylic fatty acid mixture with a chain length of 8 to 24 carbon atoms wherein the fatty acid mixture c) comprises at maximum 30 wt % of a linear C18 fatty acid, at maximum 3 wt % of fatty acids lower than C12, and at maximum 3 wt % of fatty acids higher than C18 based on the weight of a sum of monocarboxylic fatty acids.

2. The polyol ester mixture according to claim 1, having an acid value below 5 mg KOH/g, determined by ISO 660.

3. The polyol ester mixture according to claim 1 having the following fatty acid distribution:

23 to 33 wt % of a linear C18 fatty acid, 20 to 28 wt % of a linear C16 fatty acid, 10 to 18 wt % of a linear C14 fatty acid and 30 to 40 wt % of a linear C12 fatty acid with the proviso that the fatty acid mixture comprises at maximum 3 wt % of fatty acids lower than C12 and at maximum 3 wt % of fatty acids higher than C18, all % by weight based on the sum of monocarboxylic fatty acids in the reaction mixture determined by gas chromatography.

4. The polyol ester mixture according to claim 1 obtained by the esterification reaction of a) 0.9 to 1.1 mol glycerin b) 0.5 to 0.7 mol sebacic acid c) 1.1 to 1.3 mol of a monocarboxylic fatty acid mixture with a chain length of 8 to 24 carbon atoms.

5. The polyol ester mixture according to claim 1 having a tangens delta of 1 at 31±5° C., determined by oscillatory rheology with a rheometer ARG2_10H4440 of TA Instruments (Geometry: Cross Hatched—40 mm parallel plate, Peltier plate Steel—104445; measurement conditions: 15 to 50° C.; 1K/min; 0.1% Strain; 1 Hz Frequency).

6. The polyol ester mixture according to claim 1 having a melting range, measured by differential scanning calorimetry (DSC), between −25° C. and +60° C., where a width of the melting range comprises at least 30° C. and a maximum of a heatflow (W $g^{-1}$) is detected at 10±15° C.

7. The polyol ester according to claim 1, wherein the esterification reaction is carried out at temperatures of from 180 to 250° C.

8. The polyol ester mixture according to claim 1, wherein no catalyst is used in the esterification reaction.

9. A process of manufacturing a polyol ester mixture in a "one-pot-process" by reacting a) 0.8 to 1.2 mol glycerin, b) 0.5 to 0.7 mol sebacic acid, and c) 1.0 to 1.4 mol of C8 to C24 monocarboxylic fatty acids, wherein the fatty acid mixture c) comprises at maximum 30 wt % of a linear C18 fatty acid, at maximum 3 wt % of fatty acids lower than C12, and at maximum 3 wt % of fatty acids higher than C18 based on a weight of a sum of monocarboxylic fatty acids without presence of a catalyst at a temperature of 180° C. to 250° C., under vacuum removing water of reaction, until the acid value is less than 5 mg KOH/g.

10. A cosmetic or pharmaceutical composition comprising 0.5 wt % up to 100 wt % of the polyol ester mixture according to claim 1 based on the weight of the cosmetic or pharmaceutical composition.

* * * * *